(12) United States Patent
Lock et al.

(10) Patent No.: US 7,029,564 B1
(45) Date of Patent: Apr. 18, 2006

(54) DIELECTROPHORETIC APPARATUS AND METHOD

(75) Inventors: Gary Lock, Middlesex (GB); Ronald Pethig, Gwynedd (GB)

(73) Assignee: University of Wales, Bangor, Gwynedd (GB)

( * ) Notice: Subject to any disclaimer, the term of this patent is extended or adjusted under 35 U.S.C. 154(b) by 228 days.

(21) Appl. No.: 10/031,366

(22) PCT Filed: Jul. 20, 2000

(86) PCT No.: PCT/GB00/02802

§ 371 (c)(1),
(2), (4) Date: Mar. 4, 2002

(87) PCT Pub. No.: WO01/05512

PCT Pub. Date: Jan. 25, 2001

(30) Foreign Application Priority Data

Jul. 20, 1999 (GB) .................................... 9916850

(51) Int. Cl.
*B03C 5/02* (2006.01)
(52) U.S. Cl. ....................................... 204/643; 204/547
(58) Field of Classification Search ................ 204/547, 204/643
See application file for complete search history.

(56) References Cited

U.S. PATENT DOCUMENTS 5,795,457 A * 8/1998 Pethig et al. ................ 204/547
5,858,192 A * 1/1999 Becker et al. ............... 204/547
6,264,815 B1 * 7/2001 Pethig et al. ................. 204/547
6,296,752 B1 * 10/2001 McBride et al. ............. 204/547
6,875,329 B1 * 4/2005 Washizu et al. ............. 204/547
6,936,151 B1 * 8/2005 Lock et al. .................. 204/547
2001/0047941 A1 * 12/2001 Washizu et al. ............. 204/547
2002/0036141 A1 * 3/2002 Gascoyne et al. ........... 204/547

FOREIGN PATENT DOCUMENTS

WO    WO 97/34689 A1 * 9/1997
WO    WO 98/04355 A1 * 2/1998
WO    WO 99/17883 A1 * 4/1999

OTHER PUBLICATIONS

Talary et al, "Electromanipulation and separation of cells using traveling electric fields," J. Phys. D. Appl. Phys., vol. 29, pp. 2198-2203, (1996).*

* cited by examiner

*Primary Examiner*—Alan Diamond
(74) *Attorney, Agent, or Firm*—Breiner & Breiner, L.L.C.

(57) ABSTRACT

In a dielectrophoretic cell having an array of electrodes and means to apply electrical signals to the electrodes. The electrodes include a planar array of serpentine or zig-zag electrodes with their curvatures in register. The serpentine electrodes may be sinusoidal, half sinusoidal, or elongated "C" in shape. The positions of maximum curvature of each serpentine or zig-zag electrode may be arranged in linear alignment, or along a curve. The cell may be used for stationary or traveling wave dielectrophoresis. Particles traveling in opposite directions in traveling wave dielectrophoresis can do so without interference, allowing "traffic control". Particles can be characterized and separated, and particles at high concentrations, or particles of different types, can be handled.

3 Claims, 10 Drawing Sheets

DIELECTROPHORETIC APPARATUS AND METHOD

This invention relates to an apparatus and method of using the technique of dielectrophoresis, and relates particularly to an arrangement for concentrating or diluting or transporting or separating or detecting or characterising particles.

The technique of dielectrophoresis (DEP) is described in the book "Nanotechnology in Medicine and the Biosciences", Ed R R H Combs and D W Robinson, published by Gordon & Breach, Amsterdam, chapter 11 by Ronald Pethig, especially pages 88 to 93. Dielectrophoresis is the movement of particles in non-uniform electric fields. Unlike electrophoresis, charges on the particle itself are not necessary for the effect to occur and AC rather than DC fields are employed.

When an electric field is applied to a system consisting of particles suspended in a liquid medium, a dipole moment is usually induced in each particle as a result of electrical polarisations forming at the interfaces that define their structure. If the field is non-uniform, the particles experience a translational force, known as a dielectrophoretic force, of magnitude and polarity dependent on the electrical properties of the particles and their surrounding medium. This force is also a function of the magnitude and frequency of the applied electric field.

One application of the technique of DEP is described in WO 98/04355, British Technology Group, in which a particle-containing liquid is caused to flow over a comb-like array of electrodes to which signals at different frequencies are applied; particles of different characteristics are urged preferentially towards or away from different DEP regions of the array, so that the particles can be characterised. A flowing fluid is used.

The technique of travelling wave DEP is also described by Pethig, chapter 11, pages 93 to 97. One use of the technique is described in WO 97/27933, University of Texas, in which a particle-containing liquid is caused to flow through a flat cell over an array of comb-like electrodes to which signals at different phases are applied so that by a combination of travelling wave DEP, levitation, and field flow fractionation, separation and characterisation of the suspended particles is possible. A flowing fluid is used.

In conventional (i.e. using stationary rather than travelling or rotating fields) DEP, it is also known to use castellated electrodes of the type illustrated in FIG. 1, in which each electrode 10 comprises a straight linear backbone 12 having arranged alternately on opposite sides semi-circular protrusions 14. Alternatively, the protrusions can be essentially square in shape. In an electrode array, the protrusions 14 on neighbouring electrodes can be aligned as illustrated, or offset. The electrodes are used for conventional DEP, i.e. for non-travelling fields.

Throughout this specification, the term "particle" is used to include biological cells, bacteria, viruses, parasitic microorganisms, DNA, proteins, biopolymers, non-biological particles, or any other particle which may be suspended in a liquid, in which a dielectrophoretic force can be induced. It also applies to chemical compounds or gases dissolved or suspended in a liquid.

According to the invention, a dielectrophoretic cell comprising an array of elongated electrodes, and means to apply at least one electrical signal to the electrodes, in which each electrode has a notional central axis along its direction of elongation, the electrode having one or more deflections from the notional central axis, and the electrodes in the array being in register.

In the Shorter Oxford Dictionary, "deflection" is defined as "1. The action of bending down—bent condition; a bend or curve. 2. The action of turning, or state of being turned from a straight line or regular course."

In one example, the electrodes are serpentine in shape with their curvatures in register. In another example, the electrodes are zig-zag in shape with their points in register.

In one example, the electrodes in an array are all identical and parallel to each other. In another example, the shape of the electrodes alters gradually along the array.

Also according to the invention, a dielectrophoretic method comprising placing a suspension of particles in a liquid in the vicinity of an array of electrodes, the array being defined and applying at least one electrical signal to the array whereby particles are included in or excluded from regions of the electrodes corresponding to the maximum electrode curvatures. Alternatively, particles may be included in or excluded from regions of the electrodes corresponding to minimum electrode curvatures.

Weiss and Thibodeaux in US Pat. No. 4,534,856 describe an electrodynamic method for separating components such as grain and dust in agricultural by-products. This separation of components is achieved by electrically charging them above a set of parallel electrodes that generate an electric travelling wave. This travelling wave is produced by energising the electrodes using a 60 Hz, 3-phase, high voltage generator and applied voltages of up to 10,000 Volts and more. The forces acting on the component particles in U.S. Pat. No. 4,534,856 are electrostatic in nature, involving the action of electric fields on charged bodies, rather than dielectrophoretic forces described in this present invention, where high frequency signals in the range from around 1 kHz to 100 MHz, and modest voltages in the range 1–20 Volts only, are employed.

WO 97/34689A1 describes apparatus for manipulating particles along channels using dielectrophoresis. FIG. 3 shows an electrode arrangement of the so-called interdigitated, castellated type. This is not a serpentine geometry. The castellations are designed to generate highly non-uniform field patterns that can readily capture particles at the electrode castellation edges by positive dielectrophoretic forces. The effect of the castellation is not to produce the traffic control or particle sieving effects which can be achieved by the apparatus and methods of the present invention.

WO 98/04355A1 describes a method for characterising how particles respond to dielectrophoretic forces over a wide frequency range using just one test. The particles are suspended in a chamber containing an array of electrode elements, as shown in FIG. 3 of WO 98/04355A1. Each electrode is energised at a different electrical frequency, in order to generate a wide range of different dielectrophoretic forces. The dielectrophoretic response over this range is determined by inspecting how the particles are either attracted towards or repelled from each electrode element. WO 98/04355A1 does not employ the travelling electric fields or the traffic control effects which can be achieved using the methods of the apparatus and present invention.

U.S. Pat. No. 5,795,457A describes a method for manipulating particles using stationary dielectrophoretic forces—travelling electric fields are not employed. FIG. 1B(1)(a) in U.S. Pat. No. 5,795,457A shows one of the electrode arrangements that can be used, namely the so-called interdigitated, castellated, design. This is the same electrode geometry shown in FIG. 3 of WO 97/34689A1, and, as stated above, this is not a serpentine geometry. The castellation are designed to generate highly non-uniform field patterns that can readily capture particles at the electrode castellation edges by positive dielectrophoretic forces. The effect on the castellation is not to produce the traffic control or particle sieving effects which can be achieved by the methods and apparatus of the present invention.

The invention will now be described by way of example only with reference to the accompanying drawings in which:

FIG. 1 illustrates a catelled electrode of the prior art;

FIG. 2 indicates schematically a travelling wave dielectrophoretic (TWD) system;

FIGS. 3A, B, C, D, E, F and G indicate various arrangements of TWD electrodes;

FIGS. 4A, B, C, D, E and F are successive photographs of an experimental separation of particles by TWD;

Figure 1:
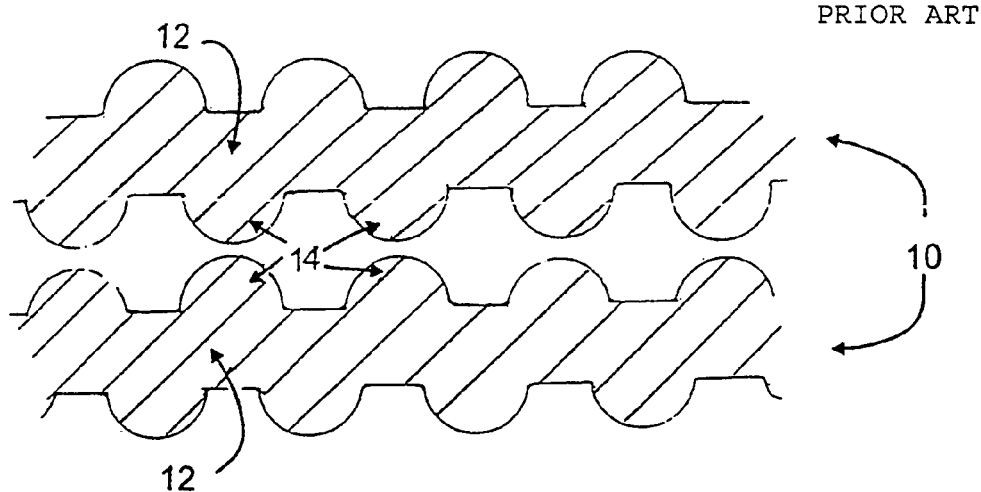
Figure 2:
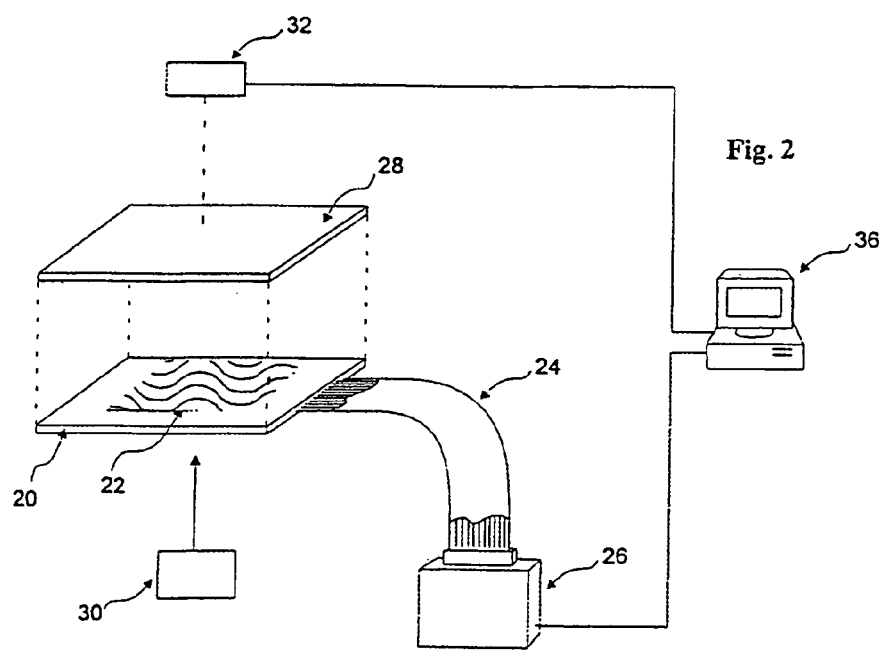

In FIG. 2, a glass substrate 20 has on its upper surface an array 22 of serpentine electrodes, each of which is connected by a multiple connector 24 to a signal generator 26. The substrate 20 can be covered by a protective cover 28 (conveniently a second glass substrate), the substrates being separated by a spacer, not shown, to form a thin cell. A suitable spacer is a plastic strip. In a variation (not illustrated), the electrode array 22 may be fabricated on the protective cover 28.

The DEP cell is illuminated from below by a light source 30, and is viewed from above by an optical microscope/video recorder 32 connected to a display screen 36.

In use, a suspension of particles in a liquid is placed on a substrate 20 and the cover 28 put into place. The signal generator 26 is arranged to apply signals of different phases to the electrodes in the array 22. For example, the signal generator 26 may be a four-phase sinusoidal signal generator, connecting successive electrodes to signals of relative phase 0°, 90°, 180° and 270°, and then repeating the cycle across the whole array 22. As is well-known, such an array generates travelling wave DEP conditions. Alternatively, a stationary DEP force can be exerted on a particle by applying to adjacent electrodes in succession, sinusoidal signals in phase opposition (0°, 180°, 0°, 180°, etc.).

The DEP cell is illuminated by the light source 30 and is viewed on the screen 36. In transmission, particles will be seen as distinct areas, and their movement can be clearly seen on the screen.

It is to be noted that there need be no liquid flow through the cell.

FIGS. 3A to 3F illustrate six different serpentine electrode arrays. In each illustration, the arrows indicate the general directions of travel of the particles under the influence of the travelling wave field, and also indicate the areas of travel within the field.

Figure 3A:
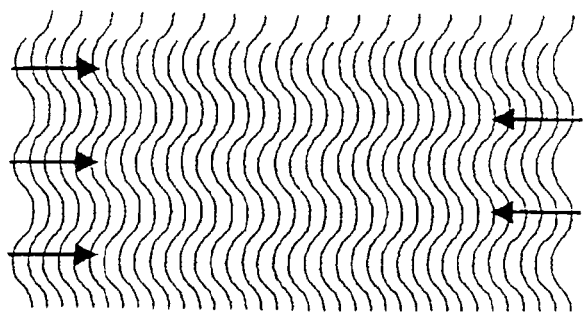

In FIG. 3A, each electrode is sinusoidal in shape. In the Figure, three sinusoidal cycles are shown, the maxima and minima of each sinusoid being in register, i.e. in alignment. The arrows correspond to these cyclical maxima and minima, showing regions in which the particles travel. Three arrows point in one direction with two arrows, intermediate the three, pointing in the opposite direction; the arrows can be regarded as indicating channels of travel, and show that simultaneous travel in opposite directions is possible by different types of particle. The arrangement can be regarded as a traffic control system—particles travelling in opposite directions do not collide.

In known travelling wave DEP (TWD) arrangements using essentially straight, parallel electrodes, the general travelling wave force is the time averaged translational travelling force which occurs perpendicular to the electrodes.

In the serpentine electrode arrays according to the invention, the general travelling wave force is indicated by the arrows; the force "concentrates" the particles into certain regions and disperses them from other regions depending on electrode shape. Put another way, the particles are included in some regions and excluded from other regions of the travelling field.

Conditions can be selected so that particles of interest travel in one direction, and other particles travel in the opposite direction.

Figure 3B:
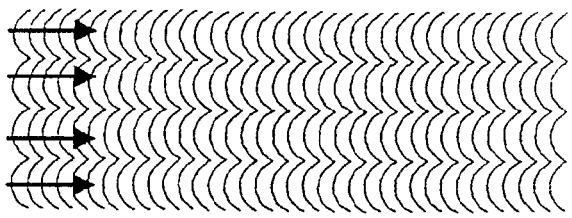

In FIG. 3B, each electrode comprises a series of half sinusoids. All of the particles travelling from left to right in FIG. 3B can be regarded as travelling in separate bands in the direction of the arrows.

Figure 3C:
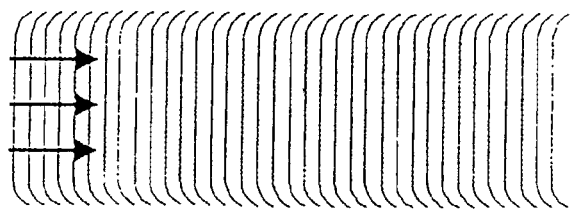

In FIG. 3C, each electrode comprises an elongated "C" shape. All of the particles travelling from left to right in FIG. 3C are excluded from the outer regions of the travelling field. This may be beneficial when there is a physical wall, at the edge of the field, thus avoiding bursting or other damage to the particles and preventing loss in the process as particles stick to the adjacent wall. An additional effect is that "clogging" as a result is reduced, i.e. the tendency of multiple particles to stick together in a clump at a wall surface may be minimised.

Figure 3D:
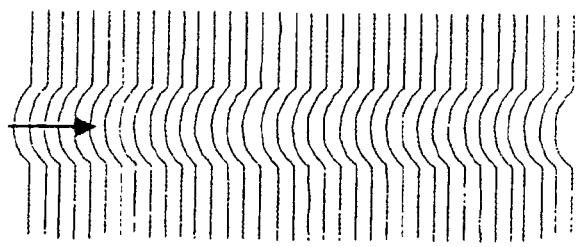

In FIG. 3D, each electrode has the form of a single half sinusoid connected between straight side arms. In this array, particles travel in correspondence with the curved part (mainly at maximum curvature). Particles travelling from right to left are excluded from the areas corresponding to the central curved part of the array. The arrangement can be regarded as a one-way channel or a valve.

Figure 3E:
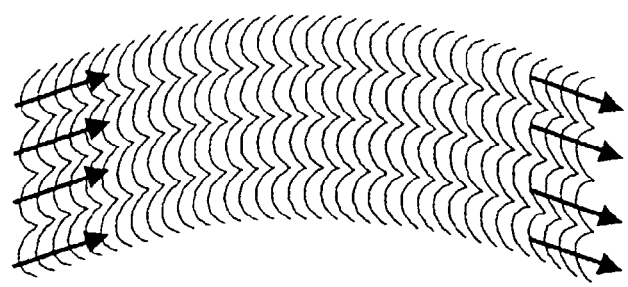

FIG. 3E is similar to FIG. 3B, except that each electrode is slightly offset from its neighbours so that the positions of maximum curvature of each electrode are arranged along parallel curves. The four channels indicated by the arrows are curved, so the arrangement can be used to guide particles round corners of smaller radius than previously possible.

Figure 3F:
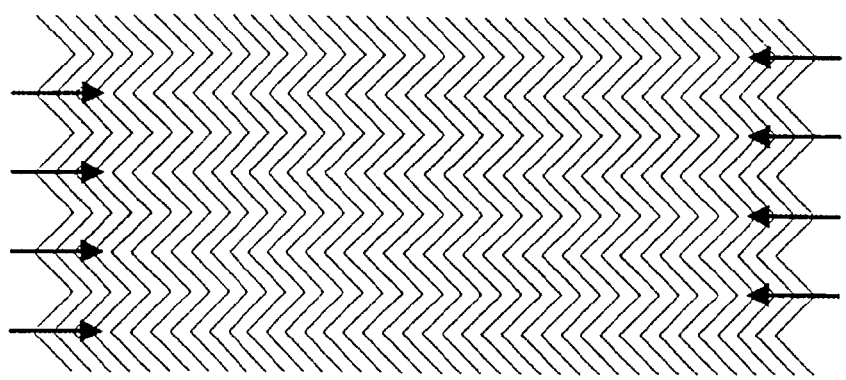

FIG. 3F is similar to FIG. 3A, except that the electrodes are zig-zag in shape instead of serpentine.

Figure 3G:
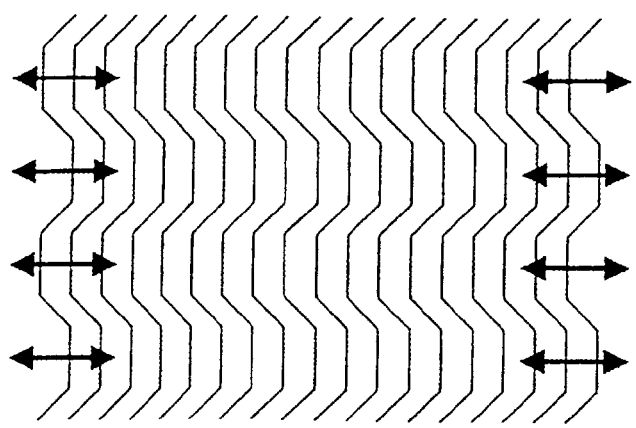

In FIG. 3G, the electrodes are straight-line approximations to the sinusoids of FIG. 3A, with each full sinusoid being represented by five straight lines; or the electrodes can be regarded as the zig-zags of FIG. 3F with flattened points. The arrows in the channels now point in both possible directions of travel, in contrast to the arrows in FIGS. 3A and 3F because particles in the straight-line part at the centre of the channels will remain in that region, regardless of the direction of travel. Particles in the 'transition' region of electrodes, i.e. between the channels, will move as illustrated in FIGS. 3A and 3F. The arrangements of FIGS. 3A and 3F are therefore preferable.

Inspection of the FIGS. 3A to 3F will show that a common feature of all the electrodes is that they have two or more different curvatures, either curves of opposite direction, or a curved part and in some cases straight portions. In another example, an electrode array could comprise a series of C-shaped electrodes, i.e. of a single curvature. Other shapes of serpentine electrodes are also possible.

By selection of appropriate shapes of serpentine or zig-zag electrode arrays, it is now therefore possible to guide travelling particles into channels, to form them into bands, to guide particles away from a mechanical constraint on the liquid flow, such as apparatus walls, and to guide them more easily round corners. Particles can be included in a particular area of the DEP field, or excluded from it. This allows particles to be accurately positioned in a travelling field, thus easing their detection. In addition, the technique can be used to guide particles towards, e.g. an antibody-coated object or surface.

FIG. 4 illustrates particle movement using the electrode array of FIG. 3A and the general arrangement of FIG. 2. Sixty four sinusoidal electrodes in an array 22 were fabricated on a glass slide 20 by photolithography, and comprise a layer of chromium covered by a layer of gold. Each electrode is approximately 10 micrometers wide and the inter-electrode spacing is about 30 micrometers in the central channel regions. A culture of live yeast cells suspended in water was used, the cell concentration being 10.2 million cells per milliliter, and the conductivity of a suspension being 10.5 mS per meter. Prior to the experiment, the electrodes were soaked in ultra pure water for over an hour to help to clean them. In the experiment, it was found that by applying a stationary DEP signal at 150 kilohertz only levitation of the particles, as a result of a negative DEP force, occurs with no translational component.

In the experiment, a stationary DEP signal at a frequency of 150 kilohertz at 3 volts peak to peak was applied to all the electrodes in the array 22. The yeast cell suspension was then applied over the electrodes and a cover slip 28 placed on top. The 150 kilohertz signal caused the particles to levitate above the electrodes and minimises sticking of the yeast cells. After a few seconds, a 50 kilohertz, 3 volt peak-to-peak travelling wave DEP field was applied; the yeast cells immediately started to move along the travelling field and started to form into bands as can be seen from FIG. 4A.

The large arrows indicate the general direction of movement of the cells, the small arrows indicate local movement of the cells as they are excluded from one channel and included in another, so that the cells form into bands. At the left hand side of the photographs, five channels are each given a channel number.

Figure 4A:
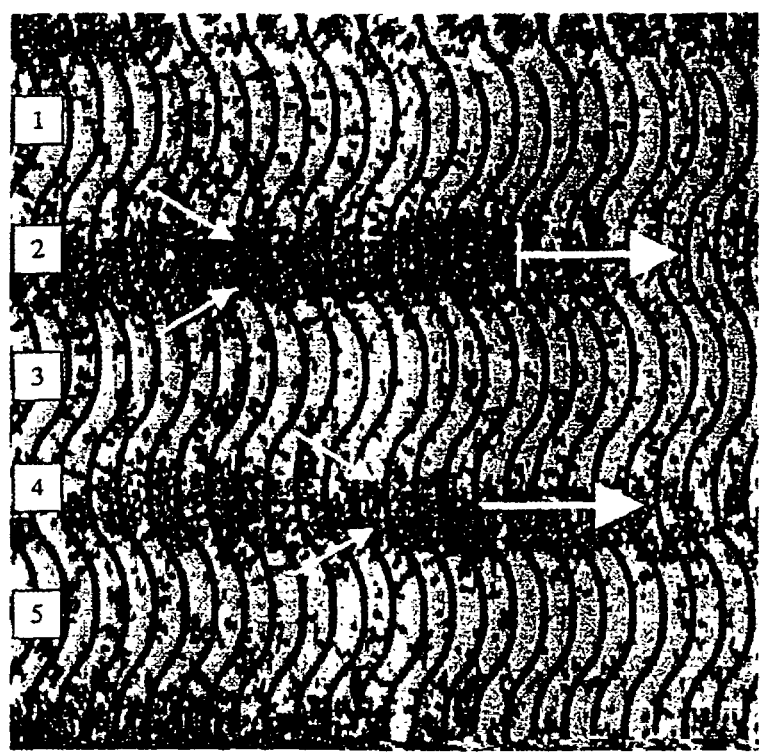
Figure 4B:
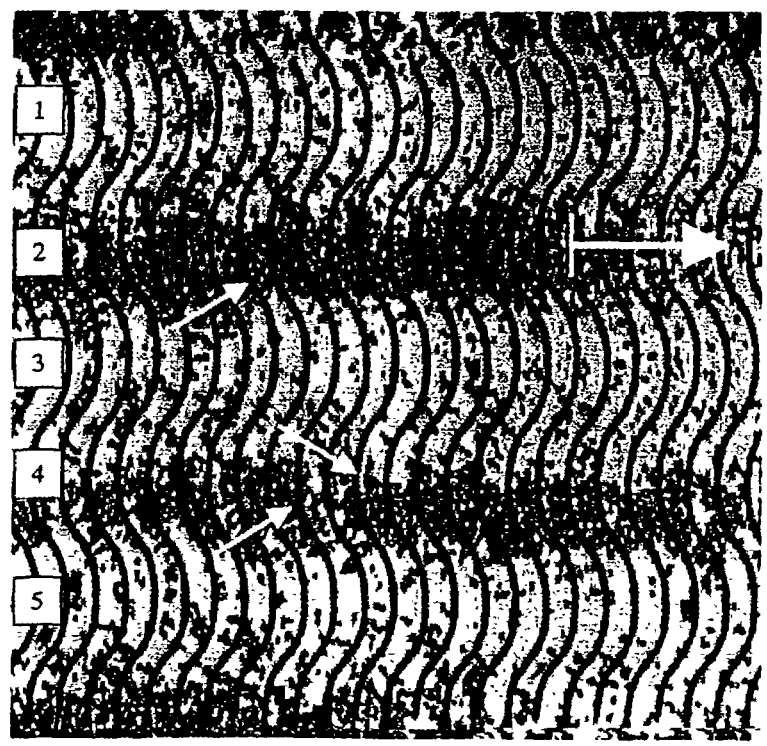

FIG. 4B is a photograph taken about three seconds after FIG. 4A; the cells can be seen to be moving to the right, and are more closely banded in channels 2 and 4, and are largely excluded from channels 1, 3 and 5.

Figure 4C:
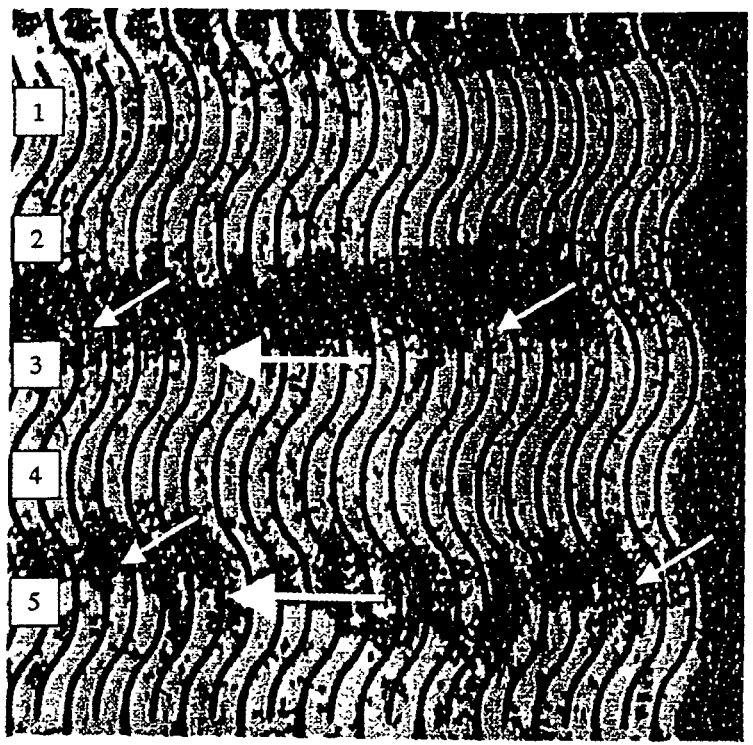
Figure 4D:
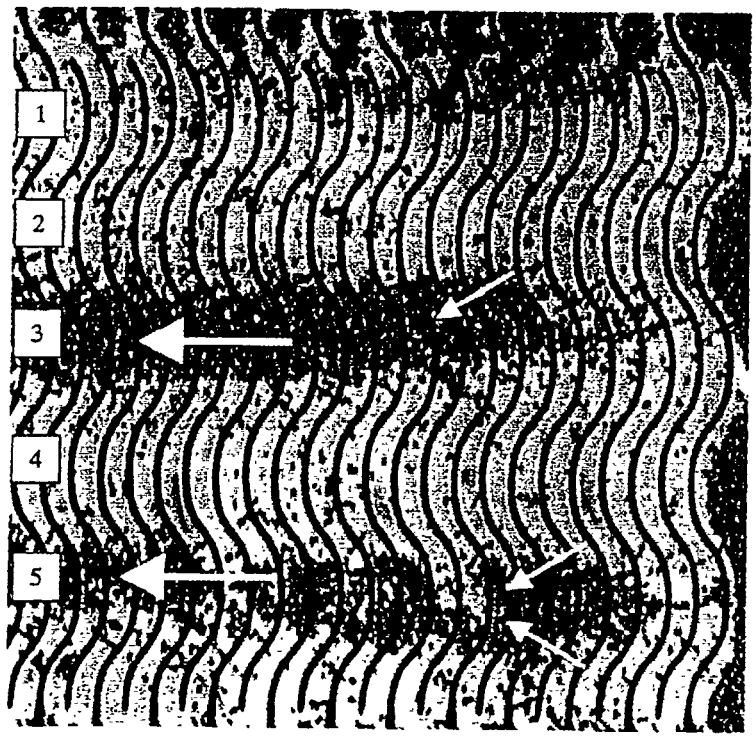

FIG. 4C was taken after the travelling wave field direction was changed. The cells are now travelling from right to left, and the bands can be seen moving out of channels 2 and 4 and into channels 3 and 5. FIG. 4D was taken three or four seconds later, and the migration into bands is even more marked.

Figure 4E:
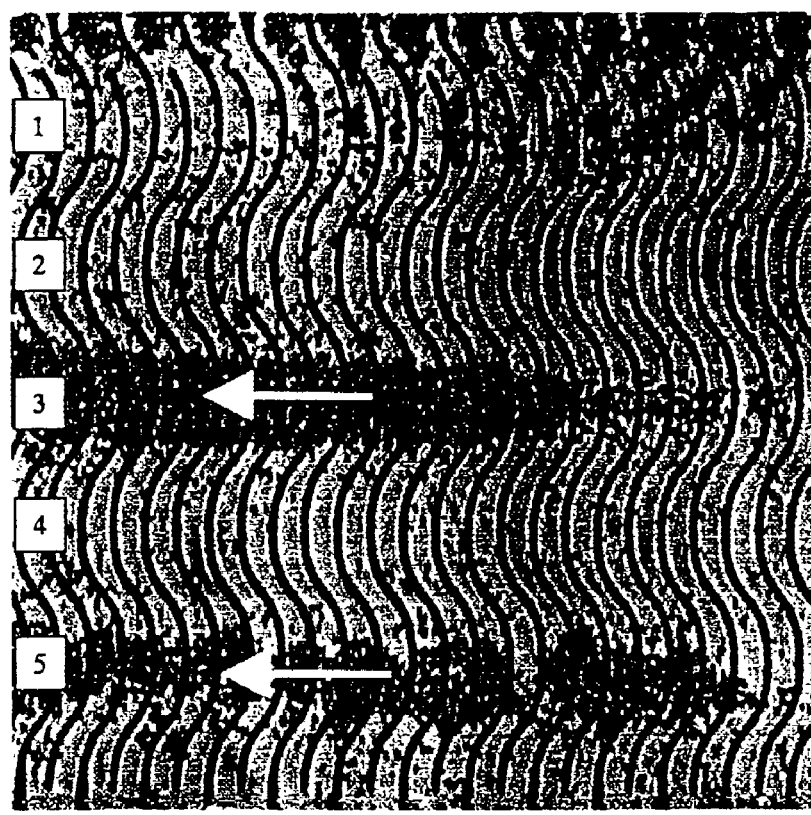

FIG. 4E shows the bands a few seconds later, and illustrates that the cell movement is beginning to leave a clear area in channels 3 and 5 as the cells are moved to the left.

Figure 4F:
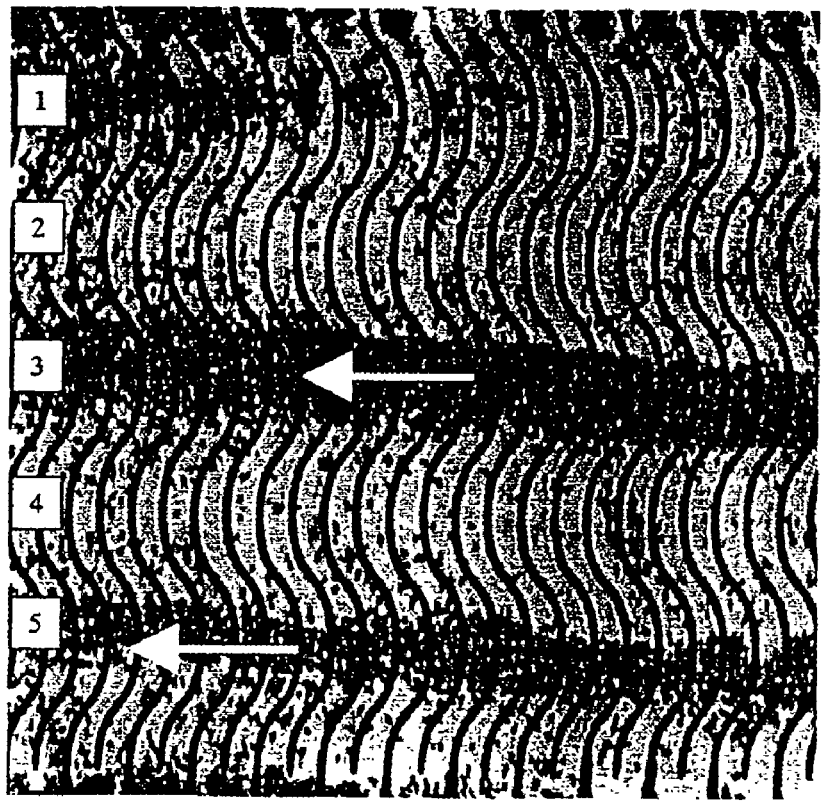

FIG. 4F is a photograph taken further along the channels to the left, showing that the bands are uniform along the channels.

The small number of cells which are speckled over the electrodes are stuck to the glass and are not moving. At such high cell concentrations, some sticking of the cells commonly occurs; this can be reduced by use of special coatings on the glass, or by using chemical agents such as surfactant or biochemical additives such as proteins (e.g. casein, denatured albumin) and using a polymeric material as a substrate, or placing a film of polymeric material over a glass substrate.

The experimental results in FIG. 4 show that particles can be formed into bands, along the direction of the travelling field and will move in those bands. At high particle concentrations, travel in bands has been found to be particularly effective. The use of serpentine electrode geometries thus permits very high particle concentrations to be handled more easily than has previously been possible using dielectrophoretic techniques.

If two particle populations are present which are of different properties, conditions can be selected so that they are caused to travel in opposite directions unhindered, allowing separation of the two types of particle. The technique works for low particle concentrations but has also been found to be particularly effective when the aggregate particle concentration is very high, such as millions or tens of millions of particles per cubic centimeter, or even higher. Useful potential commercial applications may be removing bacteria from saliva or stools; removing stem cells, foetal cells or cancer cells from blood; or removing meningital viruses from spinal fluid. In at least some of these cases, the numbers of particles to be removed may be very small compared to the numbers of particles present, so the ability to work with high particle concentrations enables separation to be effected on a practical timescale.

Experiments have been completed with human blood cells using a similar electrode arrangement to those shown in FIGS. 3A and 4. The electrodes used were 8 µm wide with 17 µm inter-electrode spacing in the central channel regions. Experiments were completed at very high cell concentrations with a dilution of 10 times of whole blood, a concentration of approximately $5 \times 10^8$ cells per milliliter (i.e., 500 million cells per cubic centimeter). Multi-phased signals were connected to the electrodes and the blood cells moved with TWD forces. A dilution of 20 times whole blood (i.e., a concentration of approximately $2.5 \times 10^8$ cells per milliliter) was found to be preferable where separation rather than just the movement of particles is desired, particularly where there is a large disparity in concentration between the cells to be separated. Disparity between cell concentrations was considerable, there being approximately 700 red blood cells for every white cell.

A particularly useful application of the serpentine electrode design involves the technique of signal superposition disclosed in UK Patent Application 9916848.6 and the International application based thereon and filed simultaneously with this application.

In one experiment, a 6 milliliter sample of human whole blood was collected in a lithium heparin tube, and within one hour was diluted 40 times in a phosphate-buffered saline solution containing sucrose, glucose, heparin and calcium chloride, to give a final suspension conductivity of 15 mS/m. The serpentine electrodes were energised with a 20 kHz, 0.6 Vrms stationary DEP signal so as to levitate the blood cells above the electrode plane when they were introduced into the test chamber. This DEP signal was then removed and two TWD signals were applied to the electrodes, one comprising a 50 kHz, 0.32 Vrms forward travelling wave and the other a 400 kHz, 0.64 Vrms reverse travelling wave. The majority of the blood cells moved rapidly along channels 3 and 5 similar to the case shown in FIG. 4f, principally under the action of the 50 kHz signal. A small number, of the order 5% or less of the total number, of the blood cells were found to be trapped on the electrodes or to move slowly along channels 2 and 4 similar to the case shown in FIG. 4a. Microscopic inspection, using a ×40 objective, indicated that approximately 20–25 red blood cells were trapped or moving in channels 2 and 4 for every white blood cell. On re-applying the 20 kHz stationary DEP signal, the trapped red blood cells were directed into channels 3 and 5 and the largest of the white cells were released and moved along channels 2 and 4. These cells appeared mainly to be neutrophils, and moved along channels 2 and 4 at a speed of the order 15 microns per second. On reducing the frequency of the reverse TWD signal from 400 kHz down to 150 kHz, the smaller white blood cells were released from the electrodes and travelled along channels 2 and 4. This cell separation process for dilute blood has been repeated for different levels of blood dilution and suspending medium composition, and it can be appreciated that in each case the specific frequency and voltage values cited above for the superimposed DEP and TWD signals were adjusted to achieve the results described above.

Another valuable attribute of the serpentine electrode design is that it can be used in a sieving action to increase cell separation efficiency. This is achieved through a cycle of operations in which, after collecting the separated subpopulation (target) cells, the main TWD signal is reversed so as to sieve out any of the target cells that may have been swept along with the main bulk of cells along channels 3 and 5. On sweeping these bulk cells in the reverse direction along channels 2 and 4, target cells that may have escaped the first separation process have the opportunity to be separated and to travel along channels 3 and 5. This process can be repeated the required number of times to achieve the desired efficiency for target cell recovery and purity of separation.

In the paper "Electromanipulation and separation of cells using travelling electric fields", J. Phys. D: Appln. Phys, 29, pages 2198–2203 (1996), Talary et al describe the separation of viable and non-viable yeast cells using TWD electrodes. The yeast cells were of the same order of size as blood cells and concentrations of approximately $1 \times 10^4$ cells per ml were subjected to TWD forces using conventional electrodes of width 10 μm and inter-electrode spacing of 10 μm. From the figures included in the publication, it can be appreciated that concentrations of the order $1 \times 10^4$ cells per ml represents close to the upper limit for the efficient manipulation and separation of cells using TWD with conventional electrode arrangements. This can be compared to the cell concentration of $2.5 \times 10^4$ cells per ml used with serpentine electrodes of the arrangement in FIG. 3a, representing an increase of 25,000 times more cells per ml. Furthermore, in the publication by Talary et al, similar ratios of differing cell types (i.e. viable and non-viable yeast) were manipulated, whereas in the manipulation of whole blood cells using serpentine TWD electrodes, the ratio of red blood cells to white blood cells was in the order of 700:1 (a considerably more complex separation). Thus by means of this invention, considerably greater particle concentrations and greater particle type disparities can be handled, and the particles separated.

By means of the arrangement of the invention, low concentration of particles may also be handled and the particles manipulated, characterised and separated with increased levels of control compared to the application of straight parallel TWD electrodes. The invention may be applied to all ranges of particle concentration to effect, although in application its benefits may be most marked when handling high concentrations.

The inventive technique also overcomes a previous disadvantage of DEP in that particles travelling along a travelling field can tend to drift—the "focussing effect" achieved by the present invention minimises such drifting. Movement under a DEP field can now be distinguished from hydrodynamic fluid flow, which can cause comparatively substantial drifting. Hydrodynamic fluid flow can be induced by heating effects caused by the electric fields.

Figure 5:
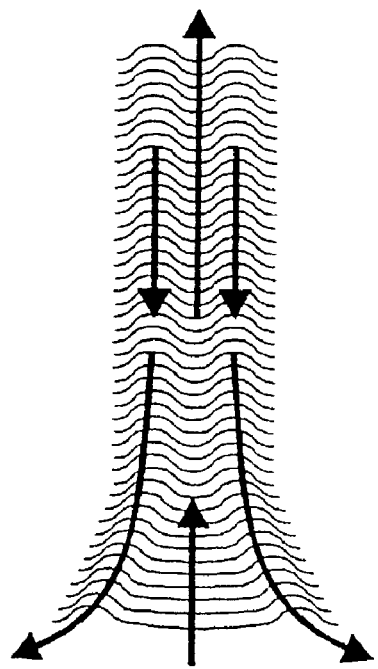
FIG. 5 illustrates an array of TWD electrodes particularly suitable for separating two particles of two or more different types.

FIG. 5 illustrates an electrode arrangement for separation of differing types of particle of different properties and different concentration. Conditions are selected so that the particles respond to the same travelling field by travelling in opposite directions; this can be achieved by changing, e.g. the properties of the applied voltage signals, or the permittivity or electrical conductivity of the suspending liquid, or changing the temperature or even adding a chemical to the suspending liquid.

As will be seen from FIG. 5, the electrodes at the upper part of the Figure are in the form of two cycles of a sinusoidal curve in register, but at the lower part of the Figure, the electrodes are in the form of two cycles separated by an almost straight part, the electrode shape gradually changing from one to the other.

In operation, the sample suspension can be introduced on to the lower part of the electrode array or placed directly on the whole electrode array. Particles of the higher concentration are arranged to move towards the top of the Figure in the central channel, while particles of the lower concentration are caused to move downwards along the two outer channels and are caused to diverge away from the central area of the array.

In practice, the particles of high concentration may trap some of the particles of low concentration and carry them upwards. This is opposite to the effect of the travelling wave DEP on the low concentration particles, and eventually they may free themselves and move into the two outer channels as required—a substantial length of the central channel maximises this possibility, for example 0.5 to 5 cm. To further assist this escape from trapping, the travelling wave field may be intermittently switched off, allowing the particles to disperse out of their band a little, and therefore assisting the lower concentration particles to escape. The same "sifting" effect can be achieved by intermittently reversing the field direction. This "sifting" effect is especially useful when working with particles which tend to clot together, such as blood cells.

The FIG. 5 arrangement may have application, for example, in separating organisms such as *salmonella* from native *E-coli* and bacteroids in a sample of stool or separating cancer cells from blood. Cell separation, using this sifting effect can also be achieved using other serpentine electrode geometries such as that of FIG. 3A or 3B.

Figure 6:
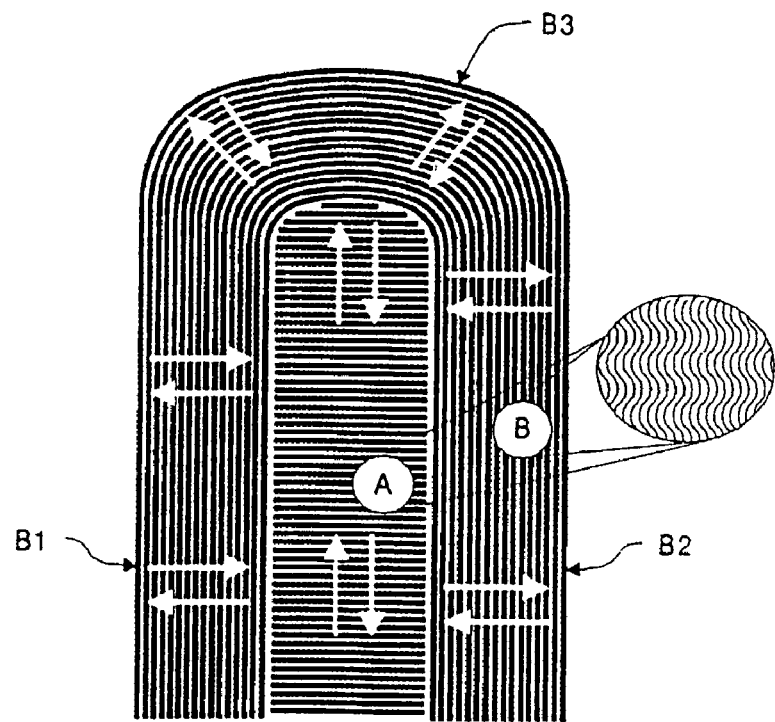
FIG. 6 illustrates schematically an alternative array of TWD electrodes.

When there is a requirement to separate or concentrate or dilute one type or more of particle in a volume of liquid and to discard a second type of particle, the arrangement of FIG. 6 can be used. The electrodes are shown as thick lines, straight or curved, but each electrode is in fact a serpentine electrode such as that illustrated in FIG. 3A.

The serpentine electrodes are arranged in two areas; a central area A, in which each serpentine electrode has a straight axis, and the axes are parallel and transverse to the Figure—as indicated in the magnified view—and an outer area B in which the axes of the serpentine electrodes are "U" shaped. The outer area B therefore has two side arms B1, B2 in which the electrode axes are straight, and a central connecting part B3 in which the electrode axes are curved.

The suspension of the mixture of particles is placed in contact with electrodes in both areas A and B, and the separation takes place in three stages:

1. Signals are applied to the electrodes in central area A so that particles of a first desired type travel downwards in the Figure and collect at the lower edge of the central electrode area, and particles of the second type travel upwards and move over the outer electrode area B. By selection of appropriate electrode shape, the particles travel in opposite directions along different channels.

2. Signals are disconnected from the electrodes in the central area A, and applied to the outer area B so that particles of the desired type travel inwards to the inner area A, and particles of the other type travel outwards and off the edges of area B and are discarded.

3. Signals to area B are disconnected and area A is reconnected, so that the desired particle type moves downwards and is collected at the bottom of the central area.

In a variation, a multi-layer fabrication technique is used, and the inner and outer areas A and B are overlaid at their edges, separated by a thin insulating layer; there is then no area in which particles may become trapped. For increased versatility of particle manipulation, different regions of electrode areas A and B may be controlled separately.

Once the technique of the invention has been applied, the separated or concentrated particle type of choice can be directed to a position at which they can be analysed or characterised by a further DEP analysis, or by any other analysis technique such as optical, ultrasonic, electrical, magnetic, PLR, FISH, etc.

In all of the described arrangements, reference has been made to placing the liquid/particle suspension on the DEP electrode array. In a first alternative, the suspension may be placed on a substrate which carries the electrode array on its opposite face. In a second alternative, the suspending liquid may first be placed on or adjacent the electrode array and the particles may be introduced afterwards; for example, in the FIG. 5 array, the particles could be introduced in the central area at the bottom of the Figure. In a third alternative, the suspension may be placed between two or more opposing electrode arrays fabricated on separate planar substrates or on a tubular substrate. However, none of arrangements depend on a fluid flow arrangement such as that used in conventional DEP. Fluid flow may be used, but it is not a requirement.

Figure 7A:
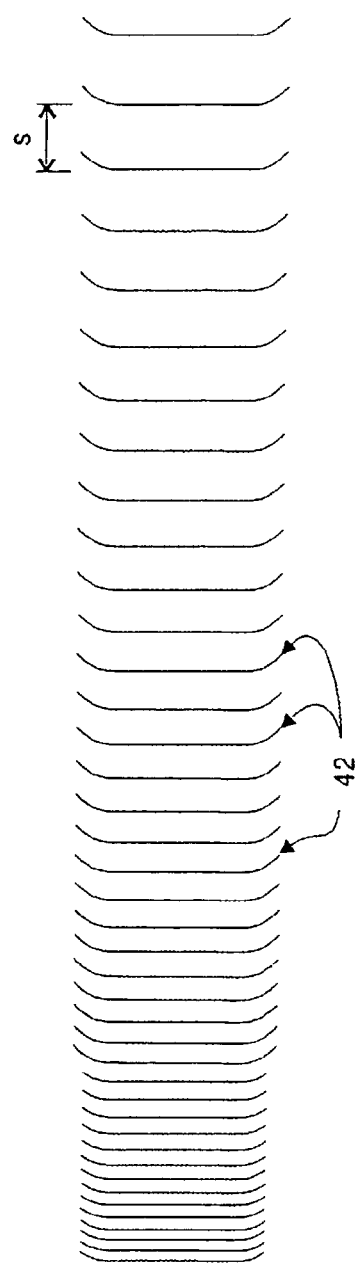
FIGS. 7A and 7B illustrate an alternative arrangement of serpentine TWD electrodes.

A further variation is shown in FIG. 7. In all previous examples, the inter-electrode spacing indicated by s on FIG. 7 has been constant, but in the variation, the mark/space ratio w/s (where w is the width of the electrode) increases along the electrode array as shown.

Figure 7B:
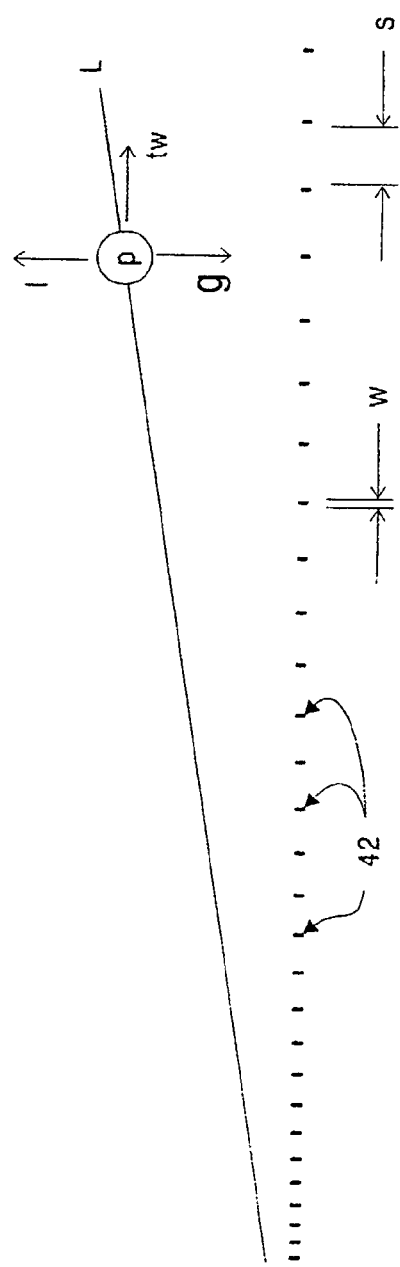

FIG. 7B gives a side view of the serpentine electrodes 42, and indicates the forces on a particle p. The result of the varying mark/space ratio is that the levitation height of particles above the electrode array, indicated by a line L, increases. The forces on a particle P are shown, i.e. an upward levitation force 1 (the real part of the travelling wave DEP force), a translational force tw (the imaginary part of the travelling wave DEP force), and gravity g. As the particle moves to the right, the translational force decreases as a result of the increasing mark/space ratio; at the same time the levitation height of the particles increases, which results in a further reduction of the translational force as the particle is further from the electrodes 42. At some point along line L, depending on particle size, the relative components of the dielectrophoretic force, the electric field strength, and electrode geometry, the translational force will become zero, so no further travel occurs. Particles of different properties will therefore travel to different distances and reside in different positions. Particle separation is therefore possible.

In a variation, initial levitation is caused either by applying a static DEP field, or by applying a TWD field at a frequency at which the particles do not experience a translational force.

Figure 8:
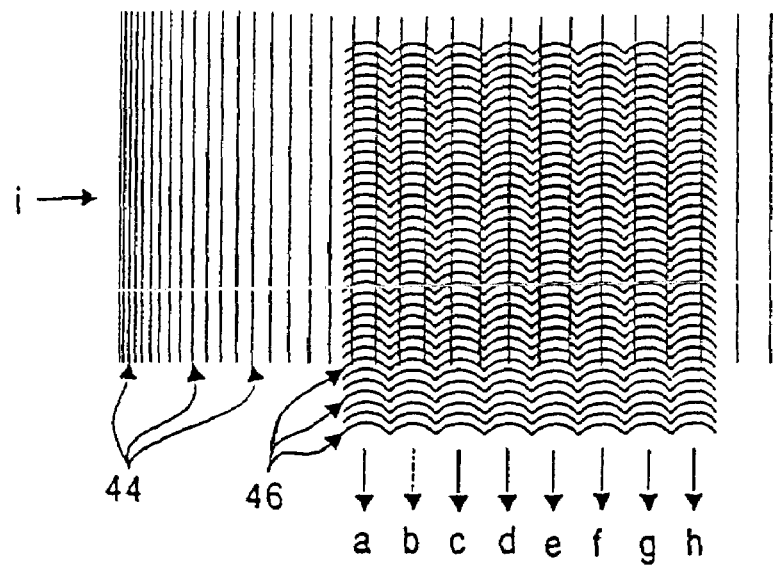
FIG. 8 shows a combination of conventional and serpentine TWD electrode arrays.

In a further variation, once particles have been separated into different regions as a result of utilising varied mark/space ratio electrodes, it is then desirable to be able to remove them selectively. FIG. 8 shows an array of varied mark/space ratio electrodes 44, in this case conventional linear electrodes, closely adjacent an array of serpentine electrodes 46 of the type shown in FIG. 3B (i.e. of constant mark/space ratio) for selective removal of particles. The arrays of electrodes may either be fabricated using multi-layer techniques, or be fabricated on to opposing substrate faces. Utilising these two electrode arrays of different geometry in combination allows particle separation as a result of differing properties, and then selective removal of the separated particles.

For example, particles may be introduced as indicated by the arrow i. Particles of differing properties will travel different distances along the array of electrodes 44, and reside in different positions. These particles may then be removed along channels 'a' through 'h' by the electrodes 46.

Numerous variants exist, using variations of serpentine, and combinations of serpentine and non-serpentine electrodes. Any of the electrode designs of FIGS. 3 and 5 may be used, or variants thereof. The choice of electrode geometries will depend on the choice of application. Changing the rate of change of the mark/space ratio of the electrodes can be beneficial depending on which particles are to be separated. For example, a linear or non-linear increase in mark/space ratio can be used. By using these variations, particles with very subtle differences may be separated and selectively removed.

Figure 9A:
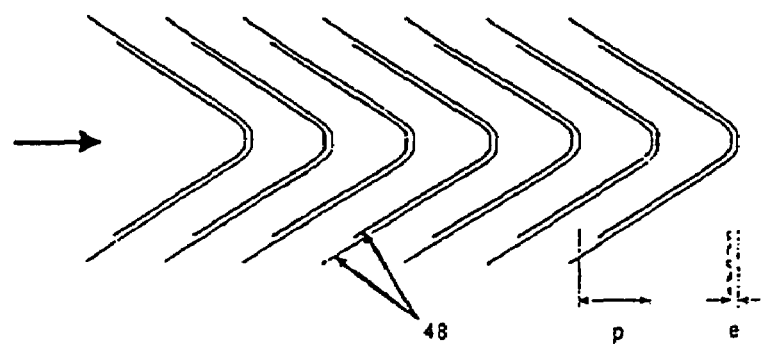
FIGS. 9A and 9B illustrate respectively an array of electrodes for static dielectrophoresis and appropriate electrical connections for the array.
Figure 9B:
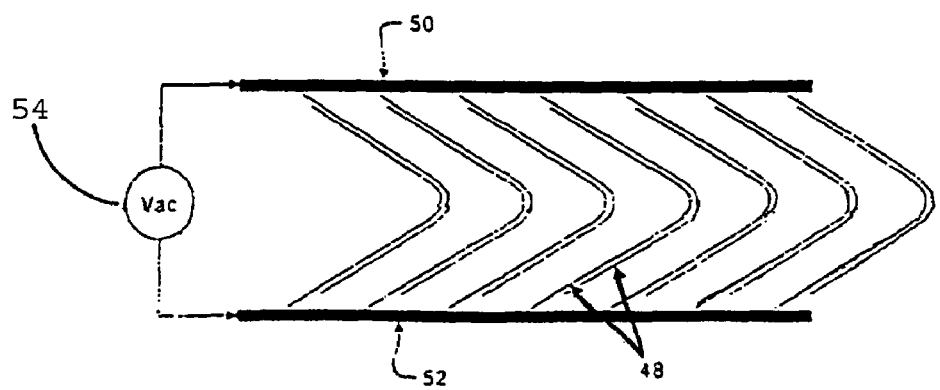

All examples described above with reference to FIGS. 2 to 8 relate to travelling wave dielectrophoresis, although the electrode arrays may also be used to apply static DEP fields. Referring now to FIG. 9, a set of serpentine electrodes suitable for static dielectrophoresis is shown. The electrodes 48 are "V" shaped and arranged in parallel pairs with the inter-electrode gap e being substantially greater than the inter-pair gap p. Each electrode in a pair projects on one side beyond the other electrode in that pair to facilitate connection to electrical connectors 50, 52 connected to opposite sides of a signal source 54.

Typically the electrodes 48 and connectors 50, 52 will be fabricated on a glass slide by photolithography, with the electrodes 48 being gold electrodes nominally 40 microns thick with an inter-electrode gap e also nominally 40 microns. Inter-pair gap p is nominally 200–1000 µm. The slide carrying the electrodes will typically be formed into a cell with a spacer and a cover as in FIG. 2, the chamber height being between 50 and 300 microns. However, for static dielectrophoresis, as is well known, a flow system must be provided by particle suspension to cause movement as indicated by the arrow in FIG. 9A. Such a flow system may be a mechanical system or flow may be caused by the well-known electrohydrodynamic effect on applying an appropriate electrical signal to the electrode array.

If the signal applied to the electrodes 48 is of such a frequency that one type of particle in a suspension flowing through the cell experiences a strong negative DEP force, according to known DEP principles, then such particles will be concentrated towards the regions of maximum curvature of the electrodes 48, while other particles flowing over the electrodes and experiencing a much weaker force, will be relatively unaffected. Particle enrichment is therefore achieved.

Figure 10:
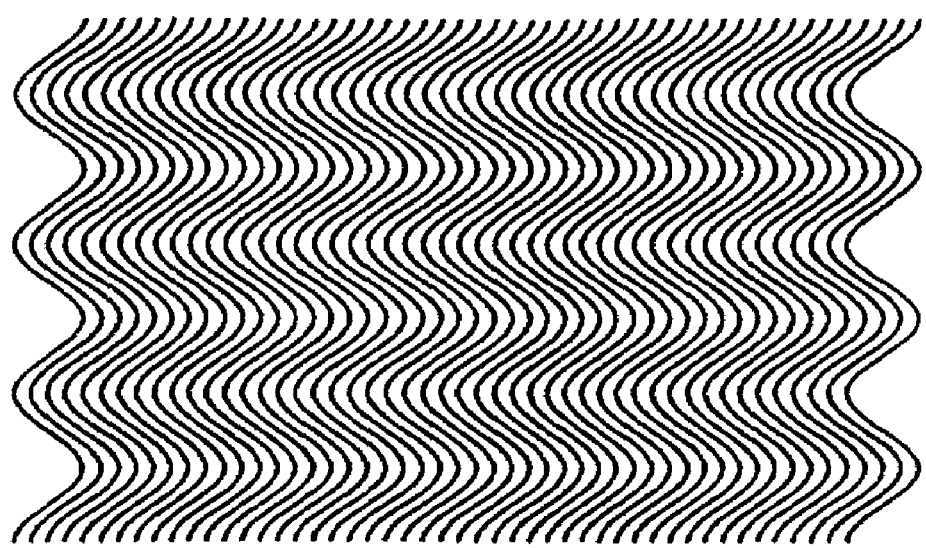
FIG. 10 shows a variation of FIG. 3A.

The arrangement of FIG. 3A refers to a traffic control system, where particles travelling in opposite directions will travel in the channel regions indicated by the arrows without colliding. FIGS. 4A to 4F show electrodes of the arrangement of FIG. 3A. These electrodes are of the form of very shallow or flat sinusoids. Alternatively, more pronounced or steep sinusoids may be used as shown in FIG. 10. From FIG. 10, it is clearly seen that the result of steeper sinusoid electrodes is more defined transition regions, i.e. the regions between the channels. It is also clearly seen that the inter-electrode gaps are significantly greater in the centre of the channels than they are in the transition regions.

The result of variations in the inter-electrode gaps across the electrode array is regional levitation gradients. In the channel regions, particles will levitate higher, while in the transition regions, they will levitate to a lower height. In the centre of the channels, the particles will levitate the highest, while in the centre of the transition region, they will be at their lowest levitation. The effects of this can be very beneficial for separations.

If a static DEP levitating field is applied, or a travelling DEP field where the translational TWD force for the particles is minimal, the particles will levitate above the electrodes and the substrate. This is beneficial for keeping the particles away from the substrate and minimising particle sticking and clogging. In practice, it is therefore preferred to apply such a field prior to application of the particles. Applying such a field to the electrodes of FIG. 10 and placing a solution of particles over them, after a few seconds it can be seen that particles concentrate in the transition regions between the channels, with the particles moving out of the channel regions due to the regional levitation gradient. Particles feeling stronger levitation forces will move more quickly. After the particles have concentrated in the transition regions, then applying a TWD field will result in particles which feel a strong TWD translational force moving into and along their respective channels. As a result of the regional levitation gradient, the channels will be predominantly free of particles, allowing particles under strong translational TWD forces to travel freely along them unhindered, improving separation efficiency.

The regional levitation gradient has further application. Particles which feel a weak translational TWD force yet a strong levitation force will still move along the dielectrophoretic cell, but the translational TWD force will be insufficient to overcome the levitation gradient. The particles will thus be restricted to movement within the transition region. This can be used to keep these particles from the fast-moving particles experiencing a strong translational TWD force in the channels. This can be considered as a secondary traffic control system in that not only are particles which are travelling in opposite directions prevented from interfering, but also fast and slow moving particles are segregated from each other. Different electrode geometries can be chosen either to enhance or to minimise this. As a further variation, this region levitation gradient can be used in conjunction with fluid flow. A small amount of fluid flow may be applied in the channel to remove particles which experience very weak or no translational TWD force. The fluid flow may be applied from a source external to the dielectrophoretic cell, or, more elegantly, a signal may be applied to the TWD electrodes which induces fluid flow, as is known. The result is that a weak fluid flow will have minimal effect on particles which experience strong TWD translational force, while particles feeling very weak or no translational TWD forces will be moved along the dielectrophoretic cell within the transition regions, thus not disrupting particles moving in the channels. The movement of particles in such a manner with hydrodynamic fluid flow may be undertaken with any of the electrode arrangements, and with or without TWD forces.

When separations are undertaken on a suspension of particles with vastly different concentrations, it is beneficial in aiding separation if conditions can be selected such that the particles are made to travel in opposite directions in a TWD field. In this case, it may be beneficial to modify the electrodes of FIGS. 3A, 3F, 4 and 10. In the figures shown, the channels for particles travelling in opposing directions are of the same width. The width of the channels may be changed to more closely reflect the disparity in concentrations of the particles travelling in them. This will make more efficient use of the electrode arrays in terms of particle movement and separation and may aid in allowing higher concentrations to be handled.

The examples have shown that serpentine or zig-zag electrodes according to the invention may be used with both stationary and travelling electric fields to both enrich and/or exclude and/or include particles from areas of the electrode array and thus areas or regions of a chamber. This has many applications for characterising, separating, and/or identifying groups of, or individual particles. Both stationary fluid or fluid flow may be used in conjunction with the electrode arrays, as may other external forces be used. Both positive and negative dielectrophoretic forces may be employed with the electrodes. Continuous separation of particles of very high concentrations is possible. By utilising these electrode arrays and predominantly negative DEP forces, no cell trapping is used, and so relatively small electrode arrays may be used to handle very large particle concentrations and very large volumes, with enrichment of the sample resulting.

The invention claimed is:

1. A dielectrophoretic (DEP) cell in which particles can be characterized, manipulated and separated comprising an array of elongated electrodes, and means to apply at least one electrical signal to the electrodes, in which each electrode has a notional central axis along its direction of elongation, each electrode has one or more deflections from the notional central axis, and the electrodes in the array being in register, wherein the electrodes are serpentine in shape, and wherein the electrodes are single half sinusoids connected between straight side arms.

2. A dielectrophoretic (DEP) cell in which particles can be characterized, manipulated and separated comprising an array of elongated electrodes, and means to apply at least one electrical signal to the electrodes, in which each electrode has a notional central axis along its direction of elongation, each electrode has one or more deflections from the notional central axis, and the electrodes in the array being in register, wherein positions of maximum curvature of each electrode are arranged in non-linear alignment, wherein the positions of maximum curvature of each electrode are arranged along a curve, and wherein the electrodes are serpentine and each electrode comprises two sinusoids, and positions of maximum curvature of the sinusoids are arranged along divergent curves.

3. A dielectrophoretic (DEP) cell in which particles can be characterized, manipulated and separated comprising an array of elongated electrodes, and means to apply at least one electrical signal to the electrodes, in which each electrode has a notional central axis along its direction of elongation, each electrode has one or more deflections from the notional central axis, and the electrodes in the array being in register, wherein the DEP cell comprises a first central array of sinusoidal or half sinusoidal electrodes, the axes of the electrodes of the first central array being straight and parallel, and a second outer array of sinusoidal or half sinusoidal electrodes, the axes of the electrodes of the second outer array being in the form of nested "U" shapes, there being provided means to apply electrical signals of different phases independently to the first and second arrays.

* * * * *